US00PP37839P2

(12) United States Plant Patent
Noordam

(10) Patent No.: US PP37,839 P2
(45) Date of Patent: Nov. 3, 2026

(54) ***CAMPANULA* PLANT NAMED 'CHAMELEON WHITE'**

(50) Latin Name: *Campanula medium*
Varietal Denomination: CHAMELEON WHITE

(71) Applicant: Jan Noordam, Waardenburg (NL)

(72) Inventor: Jan Noordam, Waardenburg (NL)

(73) Assignee: Kwekerij Stadsland (NL)

( * ) Notice: Subject to any disclaimer, the term of this patent is extended or adjusted under 35 U.S.C. 154(b) by 0 days.

(21) Appl. No.: 19/634,884

(22) Filed: Mar. 31, 2026

(51) Int. Cl.
*A01H 5/02* (2018.01)
*A01H 6/26* (2018.01)

(52) U.S. Cl.
USPC ..... Plt./414
CPC ..... *A01H 6/264* (2018.05)

(58) Field of Classification Search
USPC ..... Plt./414
CPC ..... A01H 5/02
See application file for complete search history.

*Primary Examiner* — Kent L Bell

(57) ABSTRACT

A new and distinct cultivar of *Campanula* plant named 'CHAMELEON WHITE' is disclosed, characterized by plants producing sterile flowers. The unique new cultivar produces green and white colored flowers. Flowering stems have a vase life of 18 to 22 days. Flowers on the live plants have the novel characteristic of not fading after visits by pollinators. The new cultivar is a *Campanula*, typically produced as an outdoor ornamental plant or for cut flower purposes.

2 Drawing Sheets

Figure 1:
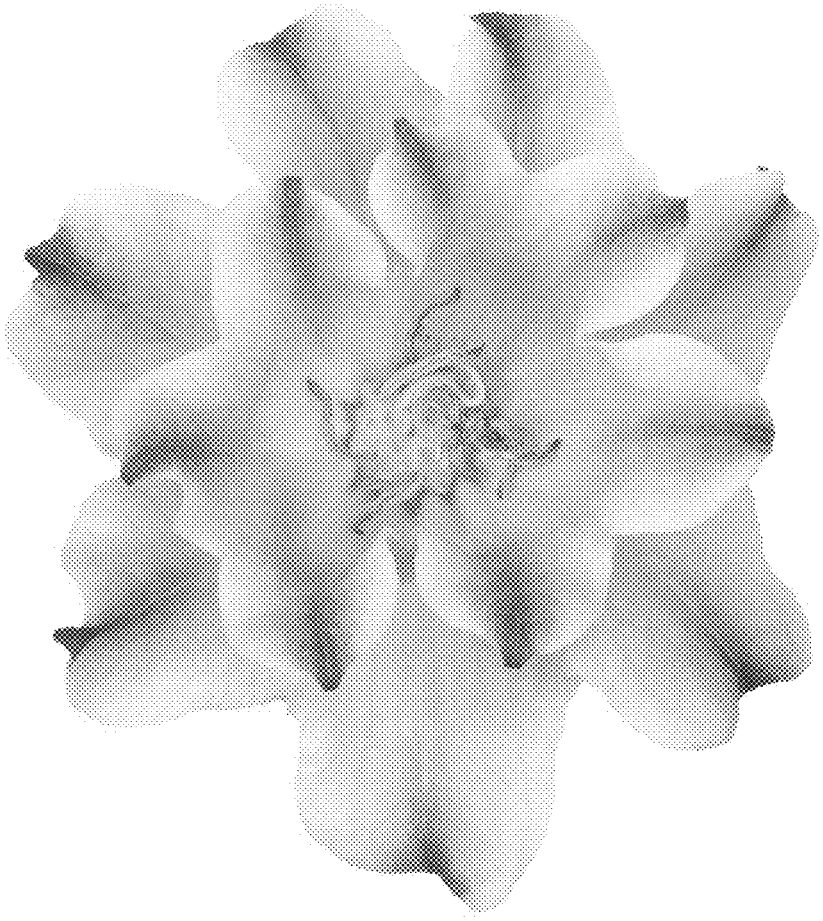

Latin name of the genus and species: *Campanula medium.*
Cultivar denomination: 'CHAMELEON WHITE'.

BACKGROUND OF THE INVENTION

The new cultivar is a product of a planned breeder program conducted by the inventor at a commercial nursery in Angeren, the Netherlands. The objective of the breeding program was to produce new *Campanula* varieties for both cut flower and garden use. The cross resulting in this new cultivar was made during June of 2021.

The seed parent is a proprietary unnamed, unpatented cultivar of *Campanula medium*. The pollen parent is a different proprietary unnamed, unpatented *Campanula medium*. The new cultivar was selected at a commercial nursery in Angeren, the Netherlands in July of 2022.

Asexual reproduction of the new cultivar 'CHAMELEON WHITE' was first performed during July of 2022 at a commercial laboratory in Heerhugowaard, the Netherlands via tissue culture. Through subsequent propagation, multiple additional generations have been reproduced, having shown that the unique features of this cultivar are stable and reproduced true to type.

SUMMARY OF THE INVENTION

The cultivar 'CHAMELEON WHITE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CHAMELEON WHITE'. These characteristics in combination distinguish 'CHAMELEON WHITE' as a new and distinct *Campanula* cultivar:

1. Sterile flowers.
2. Long lasting flowers with a vase life of 18 to 22 days.
3. Flowers do not fade after visits by pollinators.
4. Unique green and white flowers.
5. Flower color changes from more green to more white with maturity.

PARENT COMPARISONS

The new cultivar 'CHAMELEON WHITE' differs from both the seed and pollen parents in that the flowers of the new cultivar are green and white; flowers of both the seed and pollen parents are a single color. Additionally, flowers of the new cultivar are sterile; flowers of both parents are fertile.

COMMERCIAL COMPARISON

Plants of the new cultivar *Campanula* 'CHAMELEON WHITE' can be compared to the commercial cultivar *Campanula* 'Chameleon Blue', U.S. Plant Pat. No. 36,363. Plants of 'CHAMELEON WHITE' are similar to plants of 'Chameleon Blue' in most horticultural characteristics, however, plants of 'CHAMELEON WHITE' differ in the following:

1. Flowers of the new cultivar are green and white; flowers of this comparator are yellow-green, white and violet.

Plants of the new cultivar *Campanula* 'CHAMELEON WHITE' can be compared to the commercial cultivar *Campanula* 'Chameleon Light Blue', U.S. Plant Pat. No. 36,360. Plants of 'CHAMELEON WHITE' are similar to plants of 'Chameleon Blue' in most horticultural characteristics, however, plants of 'CHAMELEON WHITE' differ in the following:

1. Flowers of the new cultivar are green and white; flowers of this comparator are yellow-green, and violet.

BRIEF DESCRIPTION OF THE PHOTOGRAPHS

The accompanying drawing in FIG. 1 illustrates in full color a close-up view of a typical flower of 'CHAMELEON WHITE'.

Figure 2:
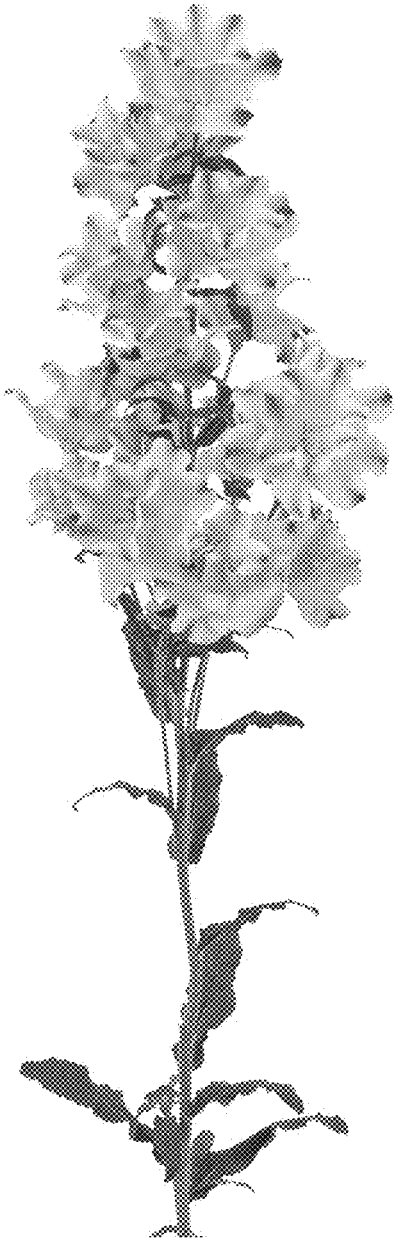

FIG. 2 illustrates a flowering stem of 'CHAMELEON WHITE'. The plant producing these flowers is approximately 250 days old, grown in the ground.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'CHAMELEON WHITE' plants grown in the ground in an unheated greenhouse in Angeren, the Netherlands from October until June. The plants were about 250 days old. Temperatures ranged from –° C. to 15° C. at night to 2° C. to 30° C. during the day. No chemical treatments were given to the plants, only biological control for thrips. Measurements and numerical values represent averages of typical plant types.

Botanical classification: *Campanula medium* 'CHAMELEON WHITE'.

PROPAGATION

Time to initiate roots: About 5 to 10 days at 15° C.

Time to produce a rooted liner: About 35 to 40 days at approximately 20° C.

PLANT

Age of plant described: Approximately 250 days.

Growth habit: Upright.

Height: 80 to 150 cm.

Plant spread: 40 cm.

Growth rate: Moderate.

Main stem characteristics:

- *Quantity.*—6 to 8 harvestable at one time.
- *Length.*—Average 140 cm.
- *Diameter.*—2.0 to 2.5 cm at base.
- *Shape.*—Round.
- *Color.*—RHS Green 140D flushed 141A.
- *Texture.*—Pubescent.

Primary lateral branches:

Quantity of primary lateral branches: 6-8.

Length of primary lateral branches: 25-30 cm.

Characteristics of primary lateral branches:

- *Form.*—Round.
- *Diameter.*—0.5-1 cm.
- *Color.*—RHS Green 140D flushed 141B.
- *Texture.*—Pubescent.

Internode length: Average range 5-7 cm.

Root description: Dense, fibrous root system. Roots variably white, not accurately measured with R.H.S. chart.

FOLIAGE

Leaf:

- *Arrangement.*—At the base very crowded (rosette). On the stems alternate.
- *Quantity.*—Approximately 200 to 300 per plant.
- *Average length.*—10 cm.
- *Average width.*—3 cm.
- *Shape of blade.*—Ovate-lanceolate.
- *Apex.*—Acuminate.
- *Base.*—Attenuate.
- *Margin.*—Serrate.
- *Aspect.*—Slightly undulate.
- *Texture of top surface.*—Glabrous.
- *Texture of bottom surface.*—Glabrous.
- *Color.*—Young foliage, upper side: Near RHS Green 141D. Young foliage, under side: Near RHS Green 141D. Mature foliage, upper side: Near RHS Green 141A. Mature foliage, under side: Near RHS Green 141A.
- *Venation.*—Type: Reticulate. Color, upper side: Near RHS Green 140D. Color, under side: Near RHS Green 140D.

Petiole:

- *Length.*—Average 5 mm.
- *Diameter.*—Average 4 mm.
- *Color.*—Near RHS Green 140D flushed 141B.
- *Texture.*—Pubescent.

FLOWER

Natural flowering season: May to June.

Inflorescence:

- *Type and habit.*—Panicle composed of single campanulate flowers.
- *Height.*—Average range 80 cm to 150 cm.
- *Diameter.*—Average range 20 to 30 cm.
- *Flowers per inflorescence.*—Average range 20 to 30.

Individual flower:

Rate of flower opening: 30 to 50 days from bud to fully opened flower.

Flower longevity on plant: 30 to 50 days.

Vase life: 18 to 22 days.

Persistent or self-cleaning: Persistent.

Flower attitude: Outward.

Bud:

- *Shape.*—Oval.
- *Length.*—2-3 cm.
- *Diameter.*—1.3 cm.
- *Color.*—RHS Yellow-Green 144D striped 144A and Green 143A and 143B.

Flower size:

- *Diameter.*—9 cm.
- *Depth.*—5 cm.
- *Throat diameter.*—2-3 cm.
- *Tube length.*—4-5 cm.
- *Tube diameter at base.*—1 cm.

Petaloid lobes:

- *Quantity.*—Typically 5.
- *Length.*—2.8 cm.
- *Width.*—2.4 cm.
- *Apex.*—Rounded. Infrequently mucronate, or with 2 rounded lobes.
- *Color.*—Opening: Upper Surface: RHS Yellow-Green 145B with a center stripe Green 143A. Lower Surface: RHS Yellow-Green 145B. Mature: Upper Surface: RHS White 155D, with a center stripe Green 143A surrounded by 145B. Lower Surface: RHS White 155D, with a center stripe Green 143C surrounded by 145B.

Petal lobes and tube:

*Petal lobes.*—Typically 5.
*Length.*—3-4 cm.
*Width.*—3 cm.
*Shape.*—Triangular.
*Apex.*—Rounded and mucronate.
*Margin.*—Entire.
*Base.*—Fused.
*Curvature.*—Strongly reflexing.
*Texture, outer surfaces.*—Petal Lobe: Soft, glabrous. Tube: Soft, glabrous.
*Texture, inner surfaces.*—Petal Lobe: Soft, glabrous. Tube: Soft, glabrous. Throat: Soft, glabrous.
*Color.*—Opening: Upper Surface: RHS Yellow-Green 145B with a center stripe Green 143A. Lower Surface: RHS Yellow-Green 145B. Mature: Upper Surface: RHS White 155D, with a center stripe Green 143A surrounded by 145B. Lower Surface: RHS White 155D, with a center stripe Green 143C surrounded by 145B. Tube when opening: RHS Yellow-Green 145B flushed 143A. No spots. Tube fully opened: RHS Yellow-Green 145B flushed 143A. No spots.

Sepals:

*Quantity.*—5.
*Length.*—1.5-2 cm.
*Width.*—1 cm.
*Shape.*—Ovate.
*Apex.*—Acuminate.
*Base.*—Obtuse.
*Margin.*—Serrate.
*Texture.*—Outer Surface: Pubescent, almost bristly. Inner Surface: Smooth.
*Color.*—Outer Surface: RHS Green 141A. Inner Surface: RHS Green 141A.

Peduncles:

*Length.*—1-2 cm.
*Diameter.*—3 mm.
*Angle.*—About 60° to the lateral branch.
*Texture.*—Pubescent.
*Color.*—RHS Green 140D flushed 141B.

Pedicels:

*Length.*—1-2 cm.
*Diameter.*—3 mm.
*Angle.*—About 60° to the lateral branch.
*Texture.*—Pubescent.
*Color.*—RHS Green 141D.

Fragrance: None.

REPRODUCTIVE ORGANS

Stamens:

*Number per flower.*—Typically 5.

Anthers:

*Shape.*—Round.
*Length.*—Approximately 1 cm.
*Color.*—Near RHS White 155C.
*Pollen.*—None.

Pistil:

*Quantity per flower.*—1.
*Length.*—Approximately 2 to 3 cm.
*Style.*—Length: Approximately 2 cm. Color: RHS White 155D.
*Stigma.*—Shape: Orbicular. Color: White 155C

OTHER CHARACTERISTICS

Seeds and fruits: Sterile; no seed production.

Disease/pest resistance: Neither resistance nor susceptibility to common diseases and pests of *Campanula* has been observed.

Temperature tolerance: Zone 8 hardiness.

What is claimed is:

1. A new and distinct cultivar of *Campanula* plant named 'CHAMELEON WHITE' as herein illustrated and described.

* * * * *